United States Patent [19]

Bier

[11] 4,362,612

[45] Dec. 7, 1982

[54] ISOELECTRIC FOCUSING APPARATUS

[75] Inventor: Milan Bier, Tucson, Ariz.

[73] Assignee: University Patents, Inc., Norwalk, Conn.

[21] Appl. No.: 99,499

[22] Filed: Dec. 3, 1979

Related U.S. Application Data

[62] Division of Ser. No. 897,261, Apr. 18, 1978, Pat. No. 4,204,924.

[51] Int. Cl.³ ............... B01D 13/02; G01N 27/26
[52] U.S. Cl. .................. 204/301; 204/180 R; 204/180 P; 204/299 R
[58] Field of Search ........... 204/301, 180 P, 180 R, 204/299 R

[56] References Cited

U.S. PATENT DOCUMENTS

| 3,657,106 | 4/1972 | Smith | 204/301 |
| 3,686,089 | 8/1972 | Korngold et al. | 204/301 X |
| 3,788,959 | 1/1974 | Smith | 204/180 P |
| 3,989,613 | 11/1976 | Gritzner | 204/180 R |
| 4,043,896 | 8/1977 | Ahlgren | 204/301 |

Primary Examiner—F. Edmundson
Attorney, Agent, or Firm—Martin Novack

[57] ABSTRACT

The disclosure is directed to an apparatus for isoelectric focusing. A fluid is employed which contains buffering compounds capable of establishing a pH gradient in an electric field. A plurality of ion non-selective permeable membranes are used to streamline the flow of fluid while allowing interchange of fluid constituents therebetween. Electrodes establish an electrical potential transverse the flow of fluid to establish a gradient of pH steps as between successive channels defined by the membranes.

6 Claims, 5 Drawing Figures

ISOELECTRIC FOCUSING APPARATUS

This is a division, of application Ser. No. 897,261, filed Apr. 18, 1978, now U.S. Pat. No. 4,204,924.

BACKGROUND OF THE INVENTION

This invention relates to techniques for the separation and/or purification of biological materials and, more particularly, to a method and apparatus for isoelectric focusing.

Isoelectric focusing ("IEF") also sometimes called electrofocusing, is an electrophoretic technique that is recognized as being a powerful method for the analysis and micropreparative separation and purification of various biological materials, including proteins, peptides, nucleic acids, viruses, and even some living cells or cell organelles. The principle of IEF is based on the fact that certain biomaterials, such as those listed above, are amphoteric in nature, i.e. are positively charged in acidic media and negatively charged in basic media. At a particular pH value, called the isoelectric point, they have a zero net charge. In other words, the isoelectric point is the pH value at which they undergo a reversal of net charge polarity. In a pH gradient such materials will migrate under the influence of a d.c. electric field until they reach the pH of their isoelectric point where they become immobilized by virtue of their zero net charge. Thus, they focus into narrow zones, defined by the pH of the medium and the electric field applied.

IEF techniques have been greatly advanced by the development of suitable buffer systems which form stable pH gradients in the electric field. Such buffers are usually composed of a random mixture of amphoteric substances having isoelectric points covering a wide spectrum of pH values. In the electric field, these components of the buffer mixture are also focused according to their isoelectric points, thereby establishing a stable pH gradient. A commercial mixture of such amphoteric substances called "Ampholine" is available from LKB Produkter AB, a Swedish Company. Other buffer systems are also compatible with IEF. The electric field in IEF thus has two simultaneous and overlapping functions; these being the establishment of the pH gradient and the focusing of the biomaterials to be separated. In terms of time sequence, the establishment of final focusing of the biomaterials cannot be achieved before a stable pH gradient is formed, i.e. before the components of the buffer mixture are focused.

While IEF is widely practiced, it is still limited by the quantities which can be processed and, to applicant's knowledge, IEF is at present used only as an analytical or micropreparative technique. There have been various prior attempts to increase the capacity of IEF. Two recent symposia, where some of the approaches were described, are as follows: (1) P. G. Righetti: Progress in Isoelectric Focusing and Isotachophoresis, North Holland/American Elsevier, 1975 and (2) J. P. Arbuthnott and J. A. Beeley, Isoelectric Focusing, Butterworth, 1975. These volumes also summarize the current status of IEF.

IEF is most often practiced in static, batch-type instruments where the fluid is stabilized by either gels or density gradients established by a non-migrating solute such as sucrose. In such instruments, the capacity for product separation is generally limited by the size of the apparatus to between 1 and 10 mg per $cm^2$ of apparatus cross-section for each component of the sample applied. Apparatus cross-section cannot be arbitrarily enlarged because of the need to dissipate the Joule heating generated by the electric field. Thus, for larger scale preparative work, it would appear that continuous flow instruments are advantageous. Unfortunately, continuous flow electrophoresis in free solutions is plagued by severe distortions of boundaries of separating materials, caused by several factors: viz., (1) The parabolic nature of liquid flow through confined channels due to viscous drag (flow is fastest through the center of the channel, and decays in a parabolic fashion towards the walls). (2) Electro-osmosis at the walls superimposes another type of parabolic flow, this being in a direction perpendicular to the parabolic profile induced by the viscous drag. (3) Density gradients arising from temperature or sample concentration gradients can cause convective flow of fluid. The disruptive effects of these three factors have been amply described in the literature (cf., for example, K. Hannig et al.: Hoppe-Seyler's Z. Physiol. Chem. Vol. 356, 1209, 1975).

To overcome these difficulties in IEF, two principles of fluid stabilization were tried: stabilization by porous media and stabilization by density gradients (see e.g. J. S. Fawcett, Annals of the New York Academy of Sciences, 209, 112–125, 1973). However, throughput was found to be only comparable to that achievable in static systems. One reason for the limited throughput is that in IEF equilibrium focusing is reached only assymptotically. The rate of electrophoretic migration of each charged species decreases progressively as it approaches its isoelectric point. At the same time, the conductivity of the system decreases as the focused components are less conductive of electricity than when far removed from their isoelectric point. Thus, to obtain sufficient focusing, a relatively long residence time is required, and this is ostensibly achievable either by low flow rates or large apparatus size. A further reason for limited throughput is the dissipation of Joule heat in continuous flow electrophoresis instruments.

It is an object of the present invention to overcome the stated prior art problems and to set forth in IEF technique which exhibits an improved capacity of product separation and purification.

SUMMARY OF THE INVENTION

The present invention is directed to a method and apparatus for isoelectric focusing of fluids. In accordance with the method of the invention, the flow of fluids to be processed is established in a first direction. This flow of fluids is streamlined by providing a plurality of permeable microporous membranes which define generally parallel channels oriented in the first direction. An electrical potential is applied across the streamlined channels of flowing fluid, and isoelectric focusing is achieved on the fluids during the flow thereof since the membranes allow interchange of fluid constituents therebetween while providing the desired streamlining. An approximation of "plug" type flow is achieved within the streamlined channels; i.e., flow having an approximately uniform cross-sectional characteristic. In the preferred embodiment of the method of the invention, a recirculation path is established for each of the streamlined channels, such that the fluid flowing out of each channel is recirculated back to the beginning of the channel. Preferably, this is achieved by pumping the fluids in each of the recirculation paths, and also providing cooling for the fluids during the recirculation thereof. In this manner, a number of "passes" are effected to obtain the desired degree of isoelectric focusing. The cooling, which is performed during the recirculation, serves to minimize problems with dissipation of Joule heat during the isoelectric focusing of the fluids in the streamlined channels. Also, in the preferred embodiment of the invention, the first direction is downward such that the streamlined fluids flow under the influence of gravity to permit gravity equilibrium of fluid levels in the channels across the streamlining membranes.

In accordance with the apparatus of the invention, there is provided an enclosure having a plurality of inlet ports for receiving the process fluids and a plurality of associated outlet ports opposing the inlet ports. Inlet and outlet separator means are provided for respectively separating the flow of fluids which enter at the inlet ports and exit at the outlet ports. A plurality of permeable membranes are disposed between respective ones of the inlet and outlet separator means and generally parallel to the direction of flow of said fluids. As previously stated, these membranes serve to streamline the flow of fluids while allowing interchange of fluid constituents therebetween. The apparatus also includes means for applying an electrical potential transverse the direction of flow of said fluids in the enclosure.

In the preferred embodiment of the apparatus of the invention, the streamlining membranes are ion nonselective microporous filters having pore sizes in the range of 0.2 to 50 microns. The spacers and membranes are preferably oriented in a vertical position, and process fluids are circulated by means of a multichannel pump operating in conjunction with a plurality of recirculation tubes which recirculate fluids from each of the outlet ports back to the corresponding inlet ports. The fluids are thus gravity fed through the enclosure. Also, in the preferred embodiment of the apparatus of the invention, cooling means are coupled to the plurality of recirculation tubes for cooling the recirculating process fluids. Means for monitoring the properties of the fluid may also be provided in conjunction with the recirculation tubes.

In accordance with a particular embodiment of the apparatus of the invention, the enclosure is defined by a stack of adjacent substantially flat parallel spacers having apertures therein which together form a cavity, and a pair of electrode compartments mounted on opposing ends of the stack, the electrode compartments defining the cavity ends. The spacers have inlet and outlet slots which define the inlet and outlet ports at opposing ends thereof, these ports communicating with the cavity. As stated, inlet and outlet separator means respectively separate the flow of fluids which enter at the inlet ports and exit at the outlet ports. These separator means may comprise, for example, separator spacers which are alternately positioned between the first mentioned spacers, the separator spacers having smaller apertures than the first mentioned spacers so that they extend into the cavity defined by the first mentioned spacers and constitute the desired fluid separating means. In this embodiment, the plurality of parallel permeable membranes are mounted in the cavity between the spacers and are operative to streamline the flow of fluids through the cavity. First and second electrode means are respectively mounted in the opposing electrode compartments, and a pair of electrode-confining membranes separate the cavity from the electrode compartments. The electrode compartments contain electrode buffer solution, and the electrode-confining membranes are of a type which does not allow free passage of fluid while readily allowing passage of electric current.

In accordance with the techniques set forth, applicant obtains the achievement of various objectives, some of which are listed as follows:

1. Provision for an apparatus and process for preparative IEF based on continuous flow principle wherein (i) stabilization of flow of the liquid against convection, (ii) stabilization of flow against electroosmosis at the walls of the vessel, and (iii) an approximation of plug flow through the apparatus are achieved by means of microporous membranes which subdivide the apparatus into a plurality of subcompartments or channels, the membranes being oriented parallel to the electrodes and parallel to the direction of flow of liquid through the apparatus.

2. Provision for an apparatus and process for IEF wherein there is an operational mode of continuous recycling of the processed fluid through the individual channels of the apparatus, and a corresponding set of heat-exchange reservoirs. This recycling mode of operation results in a separation of the function of electrophoretic focusing (carried out in the multimembrane IEF apparatus itself) from that of dissipation of Joule heat generated by the electric current (carried out in a heat exchange). This separation of functions permits scaling up of the apparatus, for it is the need to dissipate the Joule heat that limits the power input and size of most other electrophoretic equipment.

3. Provision for an apparatus and process for continuous IEF wherein unlimited residence time for achievement of final focusing equilibrium is available, independent of the size of the apparatus and rates of flow. This is achieved through the principle of repeated recycling of the processed fluid through the multimembrane IEF apparatus and the heat-exchange.

4. Provision for a process consisting of prefocusing of the buffer components in IEF before the addition of sample. The sample free-buffer can be continuously recycled until its focused equilibrium is approached. The sample is only then added. This has several advantages: (i) decreased time of exposure of the sample material to processing, which is of importance for many labile biomaterials; (ii) the possibility of adding the sample only to that compartment having a pH nearest to the isoelectric point of the desired component of the sample which can result in significant shortening of the processing time; (iii) avoidance of any extreme pH value which may again cause inactivation of labile biological materials.

5. Provision for a process for continuous flow single pass IEF, encompassing a first stage of recycling focusing of the buffer mixture to establish the stable pH gradient, followed by a single pass continuous flow focusing of the sample material.

6. Provision for an apparatus for continuous flow IEF in a recycling mode with pH and/or ultraviolet concentration sensors in at least one of the fluid flow channels for continuous monitoring of the focusing process and possible feed back control of the focusing process.

7. Provision for an apparatus and process for IEF in recycling mode whereby the voltage applied to the IEF apparatus is continuously increased as the conductivity of the buffer system decreases as a result of the focusing so as to maintain a constant power input, consistent with an allowable maximum temperature rise of the processed fluids.

DESCRIPTION OF THE PREFERRED EMBODIMENTS

The present invention is based in part on the discovery that adequate stabilization against fluid convection and wall electroosmosis can be achieved in a continuous flow IEF apparatus by subdividing the internal volume of the apparatus with a plurality of microporous membranes oriented parallel to the direction of flow of liquid through the apparatus. Fluid convection generally arises from density differences due to concentration or temperature gradients within the fluid. Concentration gradients are generally due to unequal distribution of the sample and temperature gradients arise due to Joule heating. Electroosmosis is a well known phenomenon of liquid flow along the walls of the vessels due to their electrokinetic or zeta potential. The disruptive effects on electrophoretic instruments of electroosmosis and of the parabolic flow profile have been documented, e.g. by Hannig et al. In the present invention the subdivision of the internal volume of the IEF apparatus by a plurality of membranes effectively limits the convection only to the volume elements within the individual subcompartments or channels formed between adjacent membranes. The membranes thus serve to streamline the flow of liquid through the apparatus. The membranes serve an additional important purpose; i.e., they regulate the uniformity of flow in planes perpendicular to the direction of the electric field. It is well known that due to viscous drag liquid flow through a channel assumes a parabolic flow velocity profile, provided the flow is within the regime of laminar rather than turbulent flow. Thus, liquid flow would be expected to be substantially higher near the center of a processing unit than near the electrodes. This tends to cause continuous mixing of the apparatus content. In the present invention parabolic flow is still present, but is limited to the narrow subcompartments or channels between adjacent membranes. This tends to transform what would otherwise be a parabolic flow profile to an approximation of plug flow, characterized by substantially equal flow velocity across the processing enclosure.

In the context of the present technique, plug flow and prevention of electroosmosis are important in the direction perpendicular to that of the electrophoretic migration, i.e. the direction of the electric field. Parabolic flow within any plane at equal electric potential is of lesser consequence and can be minimized e.g. by insertion of plastic screening of webbing into each membrane-defined subcompartment. There will be no electroosmosis within such a plane as it is at equal electric potential.

It is also helpful to initially distinguish between two types of electroosmosis; i.e., electroosmosis at the walls of a vessel and electroosmosis across the membranes. Electroosmosis at the walls is known to be destructive of sharpness of resolution because it tends to impose a parabolic flow profile within the chamber (e.g. Hannig et al). Microporous membranes of the type employed for the partitioning in the disclosed technique can also give rise to an electroosmotic flow in the direction perpendicular to their plane. In the context of the present technique, this electroosmosis will depend on the inherent zeta potential of the membranes themselves, which is usually minimal, but also on the pH and solute concentration gradients across the membranes. This will vary in the apparatus and is not readily predictable. It is however far less destructive of the sharpness of resolution as the flow is uniformly distributed across the whole cross-section of the apparatus and does not give rise to a parabolic velocity profile. For example, observation of colored solutions of hemoglobin in the apparatus have shown no evidence of wall electroosmosis. Electroosmosis across the separator membranes is evident as it establishes a pressure gradient across the membranes, i.e. fluid height in the various reservoirs may not be equal even at equal pumping flow rates.

The subdivision of the apparatus by means of the membranes prevents the formation of a continuous pH gradient, there being significant convection and mixing within each channel or subcompartment. Instead, a stepped gradient is obtained, the pH varying significantly from subcompartment to subcompartment.

The temperature increase of processed fluid by the Joule heat can be experimentally measured or calculated. It is well known that a watt of electric power is equivalent to 14.3 calories per minute. Knowing the power input into the IEF apparatus and the rate of liquid flow, the temperature rise is readily calculated. If the apparatus is operated at constant power, rather than constant voltage, the voltage will be progressively increasing in the early stages of focusing until a steady state is reached. The increase in voltage may result in a shift of the pH values in each subcompartment but once equilibration is reached, the voltage will remain constant, and there will be no further major drifts in pH distribution.

Figure 1:
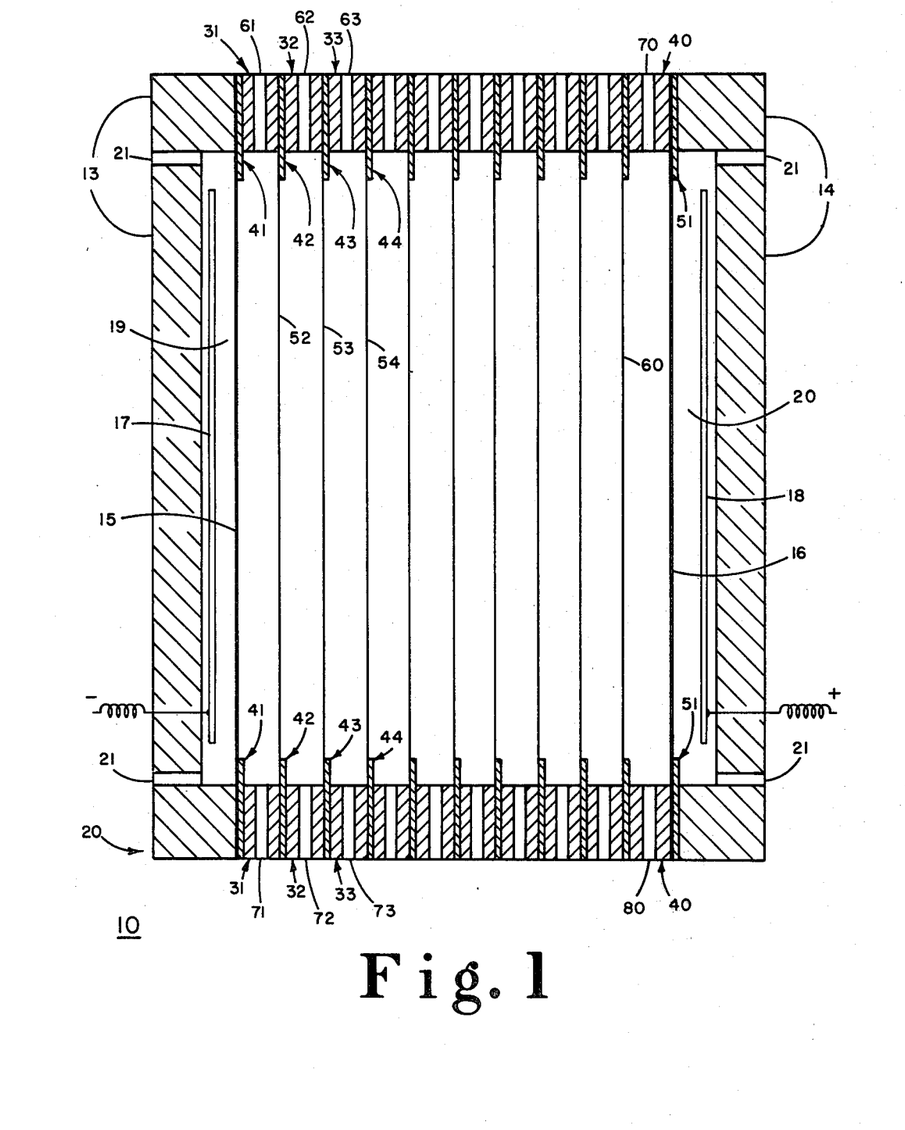
FIG. 1 is a cross-sectional view of an isoelectric focusing apparatus in accordance with an embodiment of the invention.
Figure 2:
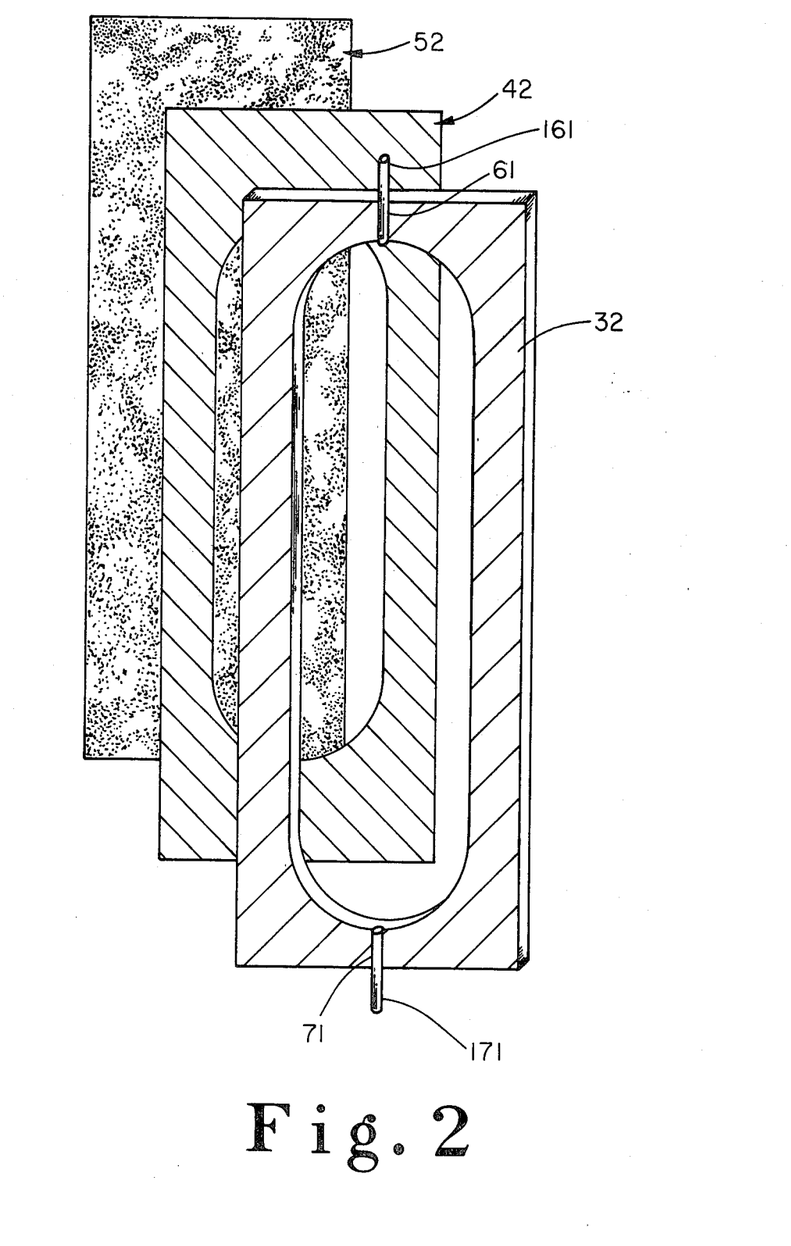
FIG. 2 is an elevational exploded view of an input/output spacer, a separator spacer, and a channel-separating membrane of the apparatus of FIG. 1.

Referring to FIG. 1, there is shown an apparatus 10 in accordance with an embodiment of the invention and which is useful in practicing the method of the invention. An enclosure 20 is defined by a stack of substantially flat parallel input/output spacers 31, 32, 33 . . . 40. In the present embodiment, the spacers are substantially rectangular in shape and have a central aperture therein, as can be seen in FIG. 2, which illustrates a representative input/output spacer 32. Between adjacent pairs of input/output spacers are located a separator spacer and a permeable membrane. There are, in the FIG. 1 embodiment, actually eleven separator spacers and nine permeable membranes, designated by reference numerals 41, 42, 43 . . . 51 and 52, 53, 54 . . . 60, respectively, with the two extra separator spacers 41 and 51 being at the ends of the stack. The separator spacers 41–51 and the membranes 52–60 may conform in their external shape to the input/output spacers 31–40, as can be seen in FIG. 2 which shows representative separator spacer 42 and membrane 52, the separator spacers 41–51 have shorter apertures than the input/output spacers, 31–40, and the permeable membranes 52–60 have no matching apertures. The spacers and membranes are clamped together, by means not shown, between a pair of end-plates 13 and 14. The end-plates 13 and 14 have recessed regions 19 and 20 which define opposing electrode compartments that house negative and positive electrodes 17 and 18. Electrode-confining membranes 15 and 16 respectively cover the compartments 19 and 20 which contain electrode buffer solutions, and ports 17 in end-plates 13 and 14 are provided for circulation of the electrode buffer solutions and venting of gaseous products of electrolysis.

Accordingly, it is seen in FIG. 1 that the apertures in spacers 31–40 and 41–51 together form a cavity, and the electrode compartments 19 and 20 on opposing ends of the stack enclose the cavity ends, so that the spacer frames and electrode compartments constitute the enclosure 20. The smaller apertures of separator spacers 41–51 mean that portions of these spacers protrude into the cavity and define separator means whose function will become apparent. Also, the permeable membranes 52–60 divide the cavity of enclosure 20 into a number of channels. Each input/output spacer 31, 32, 33 ... 40, has a respective inlet port, designated 61, 62, 63 ... 70 and a respective outlet port designated 71, 72, 73 ... 80, with the inlet and outlet ports associated with inlet/outlet spacer 32 being shown in FIG. 2. Attachment for tubing at each inlet and outlet port, as will be described, is facilitated by stainless steel needles embedded in the inlet and outlet ports, as illustrated in FIG. 2 at 161 and 171.

The illustrated number of ten channels is arbitrary and can be made greater or lesser, depending on the number of fractions desired, although at least six channels are preferred for most applications. The spacers and the end-plates can be made of non-conductive materials such as plexiglass or other polymeric compositions. The separator spacers 41–51 protrude into the cavity and provide a diffuser zone (e.g. D in FIG. 1) to permit establishment of laminar flow within each channel. These separator spacers may be formed, for example, of 0.025 cm. thick mylar. The separator membranes 52–60 should allow free flow of fluids and passage of the sample material in the fluids. They can be of filter paper, or of various types of commercially available filtering membranes or battery separator membranes, for example the 5 micron nominal pore size filter manufactured by the Millipore Corp. of Bedford, Mass. For optimal function they should have a pore size of not less than 0.2 microns, to allow free passage of fluid, and of not more than 50 microns to act as effective barriers for flow streamlining. The electrode-confining membranes 15 and 16 should have quite different characteristics, as they should not allow free passage of fluid or of the sample material but should still allow passage of electric current. Dialyzing membranes of regenerated cellulose of the type used in passive dialysis are suitable. A more preferred alternative is to use ion-selective membranes of the type used in electrodialysis. The positive electrode should be bounded by an anion permeable membrane, and the negative electrode by a cation permeable membrane. These ion selective membranes 15 and 16 have the advantage of lower passive diffusivity of ions across them as compared to cellulosic membranes, and are therefore to be preferred. The electrodes 17 and 18, can be of platinum wire, platinum foil, or any other suitable electrode material. The electrode buffer fluids may be a dilute solution of a strong acid, such as sulfuric or phosphoric acid, in the positive electrode compartment and a dilute solution of an alkali, such as sodium hydroxide, in the negative electrode compartment, as is conventional for IEF instruments.

The length of the protrusion of the separator spacers 41–51 into the cavity of enclosure 20 may be of the same order or magnitude as the width of the cavity. This provides a sufficient length of diffuser zone for avoidance of local turbulance adjacent to the inlet and outlet ports and permits establishment of laminar flow.

Figure 3:
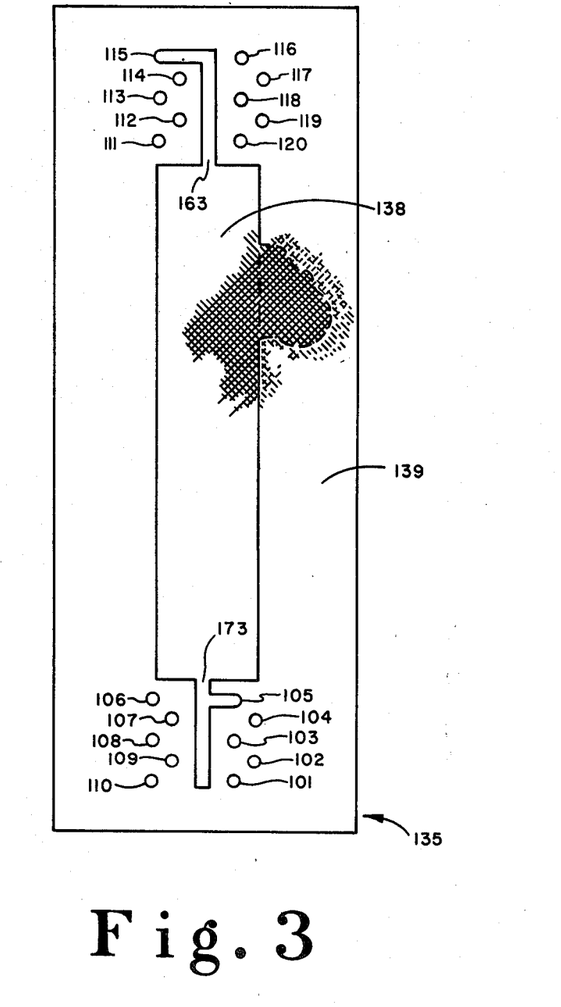
FIG. 3 is a plan view of an alternate input/output spacer.

An alternative version of the input/output spacers 31–40 is shown in FIG. 3. The spacer, designated by reference numeral 135, is formed on a screen support 118, the outside periphery of which is impregnated with a polymeric material to form the frame 139. One suitable screen material is Monodur 400 Standard, manufactured by Industrial Fabrics Corp. of Minneapolis, Minn., which is constituted by nylon monofilament of 210 microns diameter, with a mesh opening of 400 microns and overall screen thickness of 0.017". The polymeric material used for the formation of the frame 139 is applied to completely fill the mesh opening to achieve impermeability to fluid, thereby leaving the open central aperture with just screening so that fluid flow is allowed therein. The screen functions to hold the microporous membranes 52–60 (FIG. 1) roughly parallel and provide further support therefor. Each of the spacers, as 135, has an inlet port and an outlet port, these being respectively designated by reference numerals 163 and 173 in the case of the illustrated input/output spacer 135. Each such input/output spacer has provision for a plurality of flow ducts (ten in the present instance, consistent with the embodiment of FIG. 1), only one of which communicates with the aperture in each spacer via that spacer's inlet port and that spacer's outlet port. For example, the flow ducts 115 and 105, in the illustrated input/output spacer 135, communicate with the inlet and outlet ports 163 and 173, respectively. Using this scheme, each of the input/output spacers, separator spacers, and membranes of FIG. 1 would have small circular apertures or flow ducts corresponding to 101–110 and 111–120 in FIG. 3. Using this type of spacer, fluid flow may be established through the end-plates 13 (FIG. 1) which are provided with coextensive ducts and means for tubing attachment. An advantage of this type of spacer is that they permit greater flow of processed fluid than those shown in FIG. 2, as the diameter of the channels is not limited by the thickness of the spacers. It will be understood that various other spacers or structural elements can be employed consistent with the spirit and scope of the invention.

Figure 4:
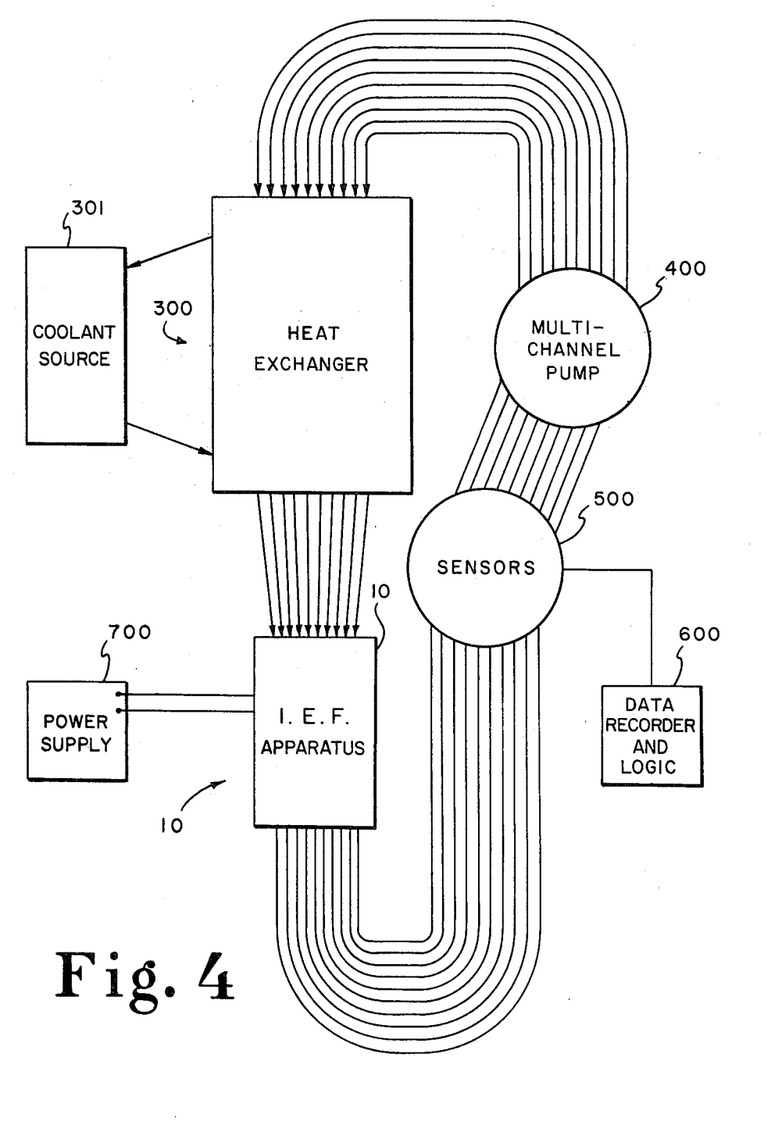
FIG. 4 is a block diagram of a continuous flow isoelectric focusing apparatus in accordance with an embodiment of the invention.

The type of apparatus illustrated in FIG. 1 is preferably employed as part of an overall apparatus or system for continuous flow IEF operation. Such a system is shown in FIG. 4 which includes an apparatus 10 (of FIG. 1) having ten input and output tubes for recirculation of the process fluids. Circulation is in closed loop fashion through a heat exchanger 300. The illustrated heat exchanger contains the same number of individual reservoirs as there are channels or compartments in the apparatus 10 (although in practice two additional reservoirs will be provided for cooling of the electrode buffer fluids). These reservoirs can be located within a single container and refrigerated by means of circulating brine from a coolant source 301. Each reservoir is coupled by suitable tubing to a corresponding port of the apparatus 10. The fluid is fed by gravity from the reservoirs to the apparatus 10. The return of the effluents from the apparatus 10 to the cooling reservoirs is accomplished by a multichannel pump 400 which may be of a commercially available type. The return lines can be provided with sensors 500 to measure the temperature, pH and/or ultraviolet absorption in one or more of the fluid streams, and can be recorded on a multichannel recorder 600, or other data collecting devices. D.C. electric current is supplied to the apparatus 10 by a power supply 700.

This system of FIG. 4 continuously recycles the contents of the individual reservoirs of heat exchanger 300 through the corresponding channels or compartments of the apparatus 10. It will be understood that a variety of data collection systems can be used, for example, visual observation, multichannel recorders, data printers, etc. The temperature of the outflowing streams can be sensed, and logic employed to regulate the power input to the apparatus 10. Such a technique would assure that the processed fluids will not be exposed to an excessive temperature rise. Moreover, as during focusing the conductivity of the fluids decreases, it will assure a maximum power input at all times, consonant with an acceptable temperature rise. Further logic can be incorporated, if desired, using sensors measuring the pH or ultraviolet absorption through each channel in conjunction with automatic control. In the preliminary stages of focusing, these parameters will be continuously changing but will reach a steady state when final equilibrium is reached, whereupon an indicating signal can be produced. It can be noted that there is some advantage in having a gravity feed into the IEF apparatus 10 and return of fluid flow to the reservoirs by means of a pump. This permits gravity equilibration of fluid levels in the channels across the membranes of the apparatus 10. Such minor fluid level differences could arise from unequal pumping rates of the multichannel pump. In other situations, one may wish to pump the fluid into the unit and return the fluid by gravity or have separate pumps to both feed and withdraw the fluid from the MSIEF apparatus. It will be understood that the described recycling mode of operation can be replaced by having a single pass continuous flow mode of operation, this being achieved, for example, by cascading two or more IEF apparatuses 10. This mode may be advantageous if ultimate equilibrium is not necessary and a relatively crude fractionation is sufficient.

Figure 5:
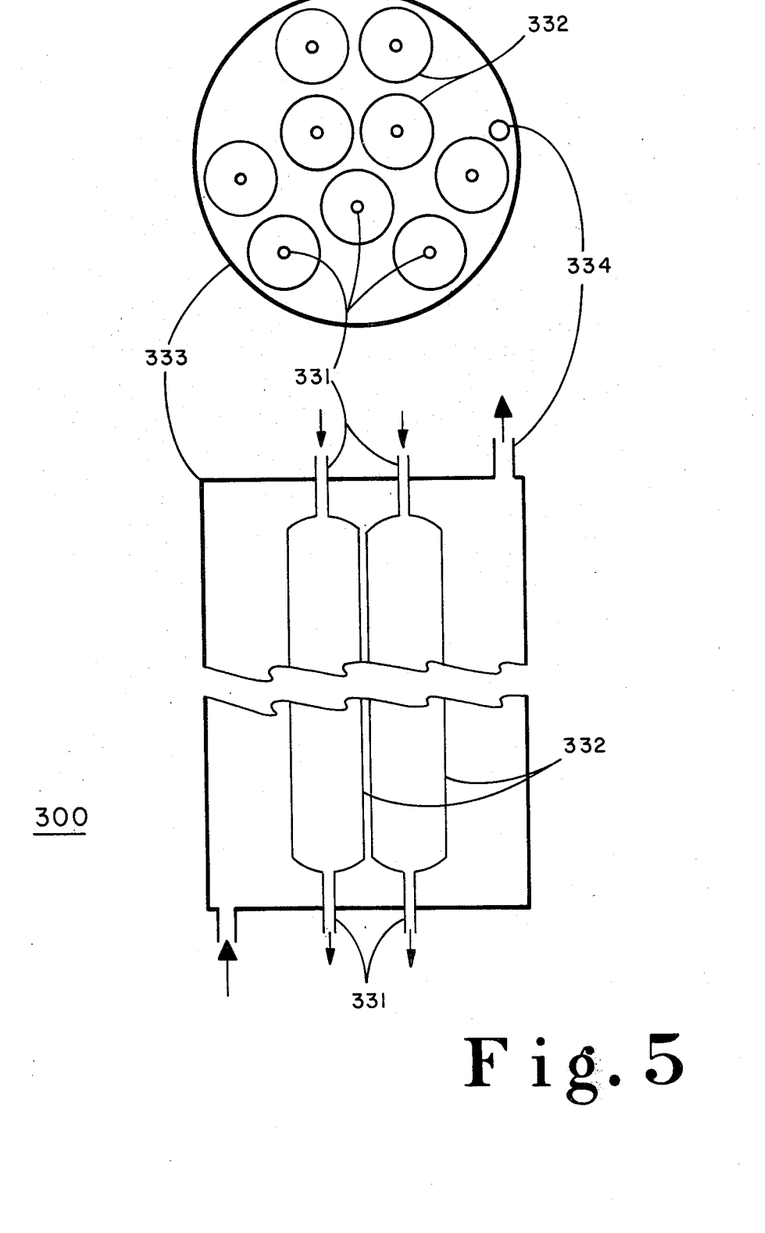
FIG. 5 illustrates, one above another, end and side views of an embodiment of the heat exchanger of FIG. 4.

FIG. 5 illustrates a possible configuration of a ten reservoir heat-exchanger 300 which can be employed in the present invention. Quick-connect ports, 331, permit easy access to the individual glass reservoirs, 332, housed within a transparent plastic enclosure, 333. Coolant circulation is provided through ports, 334. Such an arrangement permits easy visual inspection of fluid levels in each channel and any color differences arising from focusing of colored sample materials.

In a preferred mode of operation using the system described in conjunction with FIG. 4, the solutions are gravity fed from the reservoirs to the IEF apparatus 10 which is vertically oriented, i.e., its membranes are in the vertical direction. The selected buffer, suitable for establishment of a stable pH gradient, can be loaded into all but the two reservoirs used for the electrode buffers. A 0.05% to 0.5% solution of Ampholines, previously described, can be used for this purpose. Circulation through the apparatus is established and the liquid levels in the reservoirs allowed to equilibrate across the membranes of the apparatus. The remaining two reservoirs are filled with a dilute solution of strong acid for the anode compartment and a dilute solution of a strong base for the cathode compartment, as is customary for IEF techniques. These electrode rinses are allowed to flow upward through the IEF apparatus 10 to permit venting of gases generated by electrolysis. The preferred direction of flow of the processed fluid is downward through the apparatus as this is the direction of possible electrodecantation of sample materials along the membranes. To eliminate air entrapped in the IEF apparatus, the direction of pumping can be reversed during the priming procedure until all air is cleared form the tubing. After equilibration of fluid flow and temperature, electric power is applied. Typically, a gradient of 5 to 50 volts/cm is sufficient to cause rapid equilibration. The maximum power input is mainly limited by the allowable temperature rise in the apparatus due to Joule heating. Continuous or periodic temperature monitoring may be used. Typically, a reservoir temperature of 4° C. is maintained and a temperature rise of less than 10° C. will not damage most biomaterials.

It is possible to add the sample material to be focused to all reservoirs at the beginning of the operation as is common procedure in batch type operations. This will cause some of the material to be exposed to extremes of pH in the compartments adjacent to the electrodes as the pH shift is faster than the migration of the sample materials. This may damage some pH sensitive biomaterials. A preferred mode of operation is to allow at least a partial pH equilibration of the buffer to occur with the sample material added only to the channel or compartment having a pH relatively close to its presumed isoelectric point.

In practice, the heat exchanger reservoirs will have a substantially larger capacity than the internal total volume of the IEF apparatus 10. This ratio may be of the order of 10:1 to 100:1. The bigger the ratio, the longer it will require to equilibrate the contents of the reservoir. It is desirable to have sufficient flow rate to recycle the whole content of the reservoirs in one to two hours at the most, but more rapid rates of recirculation are often possible. The equilibration of the reservoirs will always lag behind the equilibration of the outflow of the IEF apparatus 10. This, once the latter is equilibrated, as attested by constancy of pH of the effluents, and/or constancy of concentration of the solutes in each effluent channel, it is not necessary to wait for the equilibration of the reservoir contents. The outflow from the IEF apparatus 10 can be simply shifted to another series of reservoirs, receiving the finally equilibrated materials. Sensing of the pH or sample concentrations can be obtained through periodic withdrawals of aliquots and measurements of pH or ultraviolet absorption, as most biomaterials absorb in the ultraviolet region. This monitoring is simplified if the system is provided with in line sensors.

Alternate modes of operation exist and may be applicable if relatively crude fractionation suffices and ultimate equilibration is not needed. One such alternate mode is to add the material to be fractionated to the system only after pH equilibration of the buffer is already achieved and then process it in single pass without recycling. Another alternate mode, as above-stated, is to avoid recycling of buffer and sample altogether and cascade the contents of the reservoirs through two or more IEF instruments 10, the sample being added either to the total volume, or at an intermediate stage, for instance between the first and second IEF apparatuses, after partial equilibration of buffer is already achieved. These modes of operation increase the throughput, as mixing within the reservoirs is avoided but are not likely to yield the same final equilibration as the recycling mode. Other similar combinations of recycling and single pass processing modes are possible.

EXAMPLE I

In this example there is demonstrated the establishment of a stable pH gradient in a sample-free Ampholine containing buffer and the subsequent focusing of a single protein in this buffer. The recycling mode was used with a 10 channel IEF apparatus of the type described in conjunction with FIG. 1. Each input-output spacer was made of plexiglass having an inside length of 24 cm, width of 2 cm, and thickness of 0.2 cm. The separator spaces were made of mylar, 0.025 cm thick, and had an inside length of 20 cm. Thus the total internal volume of the ten spacer assembly was approximately 108 ml. The twelve heat-exchange reservoirs were maintained at 4° C. and had a capacity of 125 ml each. Polyvinyl chloride battery separator membranes with a nominal pore size of 5 microns were used, manufactured by the Porvic Corp. of United Kingdom. Ion permselective membranes manufactured by Ionics Inc. of Watertown, Mass. were used as electrode membranes. A multichannel peristaltic tubing pump was used for recirculation of the processed fluids at a constant rate of approximately 1 ml/min per each channel. A constant field of 100 volts was applied across the cell, corresponding to an approximate potential of 30 volts/cm.

The apparatus was loaded with 1,000 ml. of distilled water containing 2 ml. of Ampholine, 3.5 to 10 pH range, obtained from the LKB Produkter A. B. of Sweden. This volume corresponded to about tenfold the volume of the IEF apparatus 10, each reservoir containing 100 ml. At the flow rate of 1 ml/min, about 100 min were required for complete recirculation of each reservoir. Dilute sulfuric acid and sodium hydroxide were used in the electrode compartments. At first, the apparatus was allowed to reach a focusing equilibrium with Ampholines alone, followed by the addition of 3 grams of hemoglobin into the channel #5 and its focusing determined. Hemoglobin was chosen because of its color, permitting easy visual observation and spectrophotometric quantitation. During its preparation it was saturated with carbon monoxide gas to decrease its tendency to air oxidation. Channel 5 was chosen because its equilibrated pH was distinctly different from the isoelectric pH of hemoglobin (approximately pH 7.4). The pH of all ten channels outflowing from the apparatus was periodically measured by withdrawal of aliquot samples. The pH of channels 1 and 3, outflowing from the reservoirs and inflowing into the IEF apparatus was continuously monitored by two in line pH sensors. This permitted one to determine not only the focusing in the IEF apparatus itself, but also the time necessary for the equilibration of the reservoirs themselves.

The data are presented in Table 1, column 1 listing the time of sampling, column 2 the current through the cell at 100 volts, and the remaining columns the pH of the specified flow channels.

TABLE I

| | | Equilibration of pH values in recycling IEF | | | | | | | | | | | |
|---|---|---|---|---|---|---|---|---|---|---|---|---|---|
| | Current | pH in effluent channels, number | | | | | | | | | | pH in Inflowing Channels | |
| Time | Mamp | 1 | 2 | 3 | 4 | 5 | 6 | 7 | 8 | 9 | 10 | 1 | 3 | Remarks |
| 0 | 130 | 7.1 | 7.1 | 7.1 | 7.1 | 7.1 | 7.1 | 7.1 | 7.1 | 7.1 | 7.1 | 7.1 | 7.1 | |
| 15 min | 45 | 3.21 | 4.18 | 4.48 | 5.38 | 5.88 | 6.86 | 7.13 | 9.27 | 9.74 | 9.84 | — | — | |
| 30 min | 23 | 3.08 | 4.19 | 4.48 | 5.16 | 5.70 | 6.63 | 8.07 | 9.20 | 9.46 | 9.56 | 7.51 | 8.00 | |
| 90 min | 16 | 3.26 | 4.20 | 4.49 | 5.09 | 5.57 | 6.58 | 7.53 | 8.83 | 9.07 | 9.32 | 3.79 | 5.60 | |
| 2 hrs | 13 | 3.23 | 4.24 | 4.65 | 5.33 | 5.95 | 7.00 | 7.87 | 8.99 | 9.30 | 9.58 | 3.67 | 4.93 | |
| 4 hrs | 10 | 3.09 | 4.22 | 4.75 | 5.33 | 5.85 | 7.50 | 8.64 | 8.75 | 9.14 | 9.20 | 3.25 | 4.66 | |
| 6 hrs | 10 | 2.93 | 4.21 | 4.72 | 5.32 | 5.72 | 7.08 | 8.08 | 8.49 | 8.99 | 9.33 | 3.15 | 4.76 | 3 gram hemoglobin added after this measurement |
| 6.5 hrs | 23 | 2.84 | 4.28 | 4.73 | 5.29 | 6.02 | 7.22 | 7.68 | 8.45 | 9.30 | 9.77 | 3.15 | 4.81 | |
| 7.5 hrs | 10 | 2.84 | 4.28 | 4.71 | 5.23 | 6.03 | 7.17 | 7.58 | 8.82 | 8.98 | 9.36 | 3.11 | 4.81 | |

From the inspections of pH data, it can be seen that a relatively stable pH gradient in the effluent channels is established within the first 90 minutes of recirculation. This pH gradient did not substantially change over the next 4.5 hours. Complete equilibration of the whole system required considerably longer or approximately 4 hours as indicated by the constancy of pH of inflowing channels 1 and 3 and the constancy of current consumption. This is obviously due to the unavoidable mixing of reservoir contents. Thus, while theoretically only about 100 min. would have been required for complete exchange of reservoir contents, actually this time was substantially longer. After 6 hours of continuous operation, the last two hours with a fully equilibrated system, the sample of 3 grams of hemoglobin dissolved in 30 ml. of water was added to reservoir #5. The recycling mode was shifted to a sample collection mode after 90 minutes of sample recycling without interruption of flow or current. Equilibration of the sample is accelerated by its greater density than buffer: the protein containing solutions being denser will remain layered on the bottom of the reservoirs and their remixing substantially decreased. The 90 minutes recycling were therefore sufficient for a complete recycling of each protein containing reservoir. It will be noticed that the addition of the protein caused a temporary increase of current and also a slight shift in the pH values of the protein-containing channels 6 and 7. This pH shift is due to the contribution of the protein itself to the overall buffering capacity of the processed fluid. The protein distribution in the collected ten fractions of 100 ml each was determined spectrophotometrically and was as follows:

Fractions 1–5: no detectable color
Fraction 6:2.6 gm hemoglobin/100 ml.
Fraction 7:0.39 gm hemoglobin/100 ml.
Fractions 8–10: no detectable color This example indicated that it is possible to sharply focus most of the protein sample applied into a single channel, with some overflow into a second adjacent channel. The calculated temperature rise at the beginning of the experiment, when no protein was present, was of the order of 20° C., confirmed by actual measurements. At the end of the experiment, the calculated temperature rise was less than 2° C.

hemoglobin. The data obtained after 6 and 19 hours of processing are set forth in Table III.

TABLE III

| | | Optical densities of effluent channels, number | | | | | | | |
|---|---|---|---|---|---|---|---|---|---|
| Time | Measurement | 1 | 2 | 3 | 4 | 5 | 6 | 7 | 8 |
| 6 hrs | O.D. at 541 nm | .028 | .108 | .241 | .327 | .422 | .027 | .018 | .006 |
| | O.D. at 610 nm | .023 | .227 | .083 | .048 | .134 | .007 | .009 | .007 |
| | ratio 541/610 | — | .48 | 2.90 | 6.81 | 3.15 | 3.86 | — | — |
| 19 hrs | O.D. at 541 nm | .025 | .175 | .238 | .330 | .419 | .024 | .020 | .008 |
| | O.D. at 610 nm | .020 | .235 | .085 | .051 | .132 | .017 | .014 | .006 |
| | ratio 541/610 | — | .50 | 2.80 | 6.47 | 3.17 | — | — | — |

EXAMPLE II

In this example a large scale fractionation of an artificial mixture of carbon monoxide treated hemoglobin and serum albumin was carried out. Albumin was made visible by the addition of a small quantity of Bromphenol Blue dye which stains it blue. In this case an eight channel apparatus was used, having a different type of spacer. The cavity within the spacers was 17 cm long and 6 cm wide with an effective membrane area of about 100 cm². The total internal volume of the 8 spacer apparatus was of the order of 160 ml. Together with all the tubings, pumps, etc. the total capacity of the apparatus, exclusive of the heat-exchange reservoirs was 350 ml. Plastic webbing was used to prevent excessive bulging of the membranes and aid in equilibration of liquid flow in each channel. The heat exchange reservoirs had each a capacity of 1,000 ml and a total of 8 liters was processed. This represents a 50:1 ratio of processed fluid versus internal volume of the IEF apparatus 10. The Ampholine concentration was 0.2%. After initial equilibration of the pH values in the reservoirs, a mixture of 24 gm each of albumin and hemoglobin was added only to the reservoir closest to pH 7. The expected isoelectric points of albumin is about pH 4.8, and that of homoglobin about pH 7.4. Hemoglobin is known to rapidly denature at acid pH values while albumin is more stable.

Maintaining a recirculation rate of 10 ml/min per channel, preequilibration of the buffer was allowed to proceed at 150 volts for 2 hours at which time the albumin-hemoglobin mixture was added to reservoir #5 and the fractionation continued for a total of 19 hours. The pH distribution in the effluent streams at various times is set forth in Table II.

TABLE II

| | Equilibration of pH values in recycling IEF | | | | | | | | |
|---|---|---|---|---|---|---|---|---|---|
| | pH in effluent channels, number | | | | | | | | |
| Time | 1 | 2 | 3 | 4 | 5 | 6 | 7 | 8 | Remarks |
| 45 min | 5.04 | 5.26 | 6.40 | 6.75 | 7.00 | 8.07 | 9.15 | 9.70 | |
| 75 min | 4.66 | 4.90 | 5.77 | 6.46 | 6.91 | 7.76 | 8.99 | 9.58 | |
| 2 hrs | 3.78 | 4.27 | 5.01 | 5.96 | 7.05 | 8.34 | 9.03 | 9.36 | protein added after this measurement |
| 4 hrs | 3.66 | 4.36 | 5.08 | 6.07 | 8.04 | 9.09 | 9.34 | 9.96 | |
| 6 hrs | 3.58 | 4.46 | 5.70 | 6.30 | 7.35 | 9.29 | 9.55 | 10.35 | |
| 19 hrs | 3.56 | 4.32 | 5.38 | 6.58 | 8.07 | 9.07 | 9.77 | 9.92 | |

To determine the protein distribution, optical densities of all effluents were determined with a spectrophotometer at the wavelengths of 541 nm and 610 nm. The first of these correspond to the maximum absorption of the bluish stained albumin, the second to that of the red hemoglobin.

Tables II and III indicate that equilibration of both pH and protein distribution was reached already after 6 hours processing, i.e. 4 hours after the addition of the protein. Considering the flow rate, this corresponds to a 2.4-fold recycling of the total reservoir volume of 8,000 ml. Remarkable constancy of equilibration was maintained over the next 13 hours. From the optical data, particularly the ratios of absorption at 541/610 nm, it is evident that most of the albumin was confined to channel 2 while the bulk of hemoglobin was confined to channels 4 and 5. The effluent of channel 3 was mainly hemoglobin with traces of albumin added. There is also a highly significant and consistent difference in the 541/610 ratio between channels 4 and 5. This points to a partial separation of two species of hemoglobin. The data were confirmed by analytical IEF in polyacrylamide gels. Albumin was found only in channels 2 and 3, hemoglobin in channels 3-5. While albumin gave a single blue line, hemoglobin gave a plurality of lines, the main two lines being a clearly red one, and a slightly more alkaline brownish line. It is this partial oxidation product of hemoglobin which accounted for the difference in observed ratios. Quantitation of the analytical run was not attempted. This example clearly demonstrates the relatively high capacity of the invented apparatus and process, even though the resolution of albumin and homoglobin was incomplete. It is believed that this was due to the use of only an eight channel apparatus, insufficient for complete resolution, and possible excessive protein loading.

I claim:
1. Apparatus for isoelectric focusing, comprising, in combination:
   an enclosure having a plurality of inlet ports and a plurality of associated outlet ports opposing said inlet ports;
   a plurality of recirculation paths, each coupling an outlet port to a respective inlet part;
   a fluid within said enclosure and said recirculating paths, said fluid containing buffering components capable of establishing a pH gradient in an electric field;

inlet and outlet separator means for respectively separating the flow of fluid which enters at said inlet ports and exists at said outlet ports;

a plurality of ion non-selective permeable membranes disposed between respective ones of said inlet and outlet separator means and oriented generally parallel to the direction of flow of said fluid so as to streamline the flow of fluid as between said inlet and outlet separator means while allowing interchange of fluid constituents therebetween;

means for applying an electrical potential transverse the direction of flow of said fluid in said enclosure to establish a gradient of pH steps as between successive channels defined by said membranes;

a multichannel pump for pumping the fluid in said recirculation paths;

a heat exchanger coupled to said recirculation paths for cooling the fluid therein; and sensing means coupled to said recirculation paths for sensing the properties of the fluid in said recirculation paths.

2. Apparatus as defined by claim 1 further comprising means for recording the properties sensed by said sensing means.

3. Apparatus as defined by claim 1 wherein said streamlining membranes are microporous filters having pore sizes in the range of 0.2 to 50 microns.

4. Apparatus as defined by claim 1 wherein said spacers and membranes are oriented vertically and said fluid is gravity fed to said inlet ports.

5. Apparatus as defined by claim 1 wherein said channels comprise at least six channels.

6. Apparatus as defined by claim 1 wherein each recirculation path is adapted to hold at least ten times as much fluid as its respective channel.

* * * * *